United States Patent [19]
Lestina et al.

[11] Patent Number: 5,283,163
[45] Date of Patent: Feb. 1, 1994

[54] PHOTOGRAPHIC MATERIAL AND PROCESS EMPLOYING A DEVELOPMENT INHIBITOR RELEASING COMPOUND CONTAINING A FLUORINATED CARBON ALPHA TO AN AMIDE GROUP

[75] Inventors: Gregory J. Lestina; David T. Southby; Wojciech Slusarek, all of Rochester; David A. Steele, Webster; Teh-Hsuan Chen, Fairport, all of N.Y.

[73] Assignee: Eastman Kodak Company, Rochester, N.Y.

[21] Appl. No.: 992,682

[22] Filed: Dec. 18, 1992

[51] Int. Cl.$^5$ ................................................ G03C 1/46
[52] U.S. Cl. ..................................... 430/505; 430/544; 430/957; 430/553; 430/555; 430/557; 430/558
[58] Field of Search ............... 430/957, 505, 544, 553, 430/555, 557, 8

[56] References Cited

U.S. PATENT DOCUMENTS 4,908,302  3/1990  Delpato ........................... 430/957
4,937,179  6/1990  Hirano et al. .................... 430/957

FOREIGN PATENT DOCUMENTS 167173   12/1987  European Pat. Off. .
60184248  3/1984  Japan .

Primary Examiner—Charles L. Bowers, Jr.
Assistant Examiner—Geraldine Letscher
Attorney, Agent, or Firm—Arthur E. Kluegel

[57] ABSTRACT

A photographic development inhibitor releasing compound comprises a releasable development inhibitor group comprising an amide group containing a carbon alpha to the amide functionality which is di- or trifluorinated. Such a compound is useful in photographic silver halide materials and processes to enable increased image sharpness and good interimage results.

12 Claims, No Drawings

PHOTOGRAPHIC MATERIAL AND PROCESS EMPLOYING A DEVELOPMENT INHIBITOR RELEASING COMPOUND CONTAINING A FLUORINATED CARBON ALPHA TO AN AMIDE GROUP

FIELD OF THE INVENTION

This invention relates to photographically useful compounds that release an advantageous development inhibitor compound in a photographic silver halide material upon processing and to new photographic materials and processes using such compounds.

BACKGROUND OF THE INVENTION

Images are commonly obtained in the photographic art by a coupling reaction between the development product of a silver halide color developing agent, typically an oxidized aromatic primary amine developing agent, and a color forming compound commonly referred to as a coupler. The resulting image dyes are typically cyan, magenta and yellow dyes that are formed in or adjacent to silver halide layers sensitive to radiation complementary to the color of the radiation absorbed by the image dye.

Various ways are recognized in the photographic art for improving the quality of such images produced in color photographic silver halide materials. One of the ways has been to use a compound, especially a coupler, that is capable of releasing a diffusible development inhibitor moiety as a function of silver halide development. The patent and technical literature is replete with references to compounds, particularly couplers, generally referred to as DIR compounds, that can be used for improving graininess, sharpness and tonal rendition of images in such materials. Representative compounds are described in, for example, U.S. Pat. Nos. 3,227,554; 3,701,783; 3,615,506; 3,617,291; 3,379,529; 3,620,746; 3,384,657; 3,733,201; 4,248,962; 4,409,323 and 4,782,012.

A continuing need has existed for a development inhibitor moiety that enables increased inhibitor mobility that, in turn, provides useful interimage effects and increased sharpness of the color image produced in a color photographic silver halide material. It has been particularly desirable to provide such results with a releasable azole such as a triazole or tetrazole; or a benzotriazole, mercaptoazole, mercaptooxazole, or mercaptothiazole development inhibitor containing moiety. In this regard, it has been proposed to add an amide group to a mercaptoazole inhibitor moiety, such as described in European Patent Application 157,173 and Japanese Patent Application 60-184248. The amide function, such as acetamide, alone on a mercaptoazole inhibitor moiety was not found to provide the desired results as indicated by the comparative data in the following examples.

Releasable inhibitors of the art which are weakly adsorbed to silver and silver halide have been found to be most effective in improving sharpness of a color image because their effects are wider ranging. However, because of their weak inhibition of silver development, they must be coated in higher concentrations and so effects of seasoning of the developer occur. These may be overcome by making the inhibitors self-destructing upon prolonged exposure to the alkalinity of the developer solution. However coating large quantities of couplers releasing weak inhibitors can lead to other sensitometric problems. For instance, the dye formed as a consequence of inhibitor release may give sensitometric imbalance. These can be partially overcome by so-called "universal" couplers where the dye is unballasted and washes out or reacts to form colorless products, but these, in turn, lead to a loss of imaging efficiency usually seen as a loss of speed.

The effectiveness of a DIR coupler with respect to interimage effects can be evaluated by comparing the extent to which the released inhibitor causes the desired inhibiting effect on the adjacent layer ("Receiver") compared to the extent to which it causes an inhibiting effect on the layer in which it originates ("Causer"). Intralayer diffusion of an inhibitor precursor or inhibitor enables the inhibitor to cause an increase in sharpness of the image as well as a reduction in development in that layer.

A need has existed to provide a DIR compound, particularly a DIR coupler, in a photographic material and a process that enables formation of an image having improved sharpness with useful interimage results. Such a need has been especially important for a DIR compound, particularly a DIR coupler, that enables formation of a dye that is capable of being washed out of the photographic material upon processing. Moreover, such needs have existed with the added parameter that such a DIR compound must not require significantly modifying the development inhibitor moiety or the parent coupler moiety in a way that would adversely affect the desired properties of the inhibitor moiety, the stability, the reactivity toward oxidized developer, or other properties of the image dye-forming couplers present in the photographic material and process.

SUMMARY OF THE INVENTION

The present invention solves these problems by means of a photographic element comprising at least one photographic silver halide emulsion having associated therewith at least one DIR compound containing a releasable moiety comprising a development inhibitor moiety, wherein the inhibitor moiety comprises an amide group and a carbon alpha to the amide functionality wherein said carbon is di- or tri-fluorinated.

The invention provides a photographic element, coupler, and a development process which produce an image of superior quality.

DETAILED DESCRIPTION OF THE INVENTION

A preferred amide group, as described, is represented by the formula:

$$-ArY[CF_2R]_q$$

wherein Ar is an aromatic hydrocarbon or heterocycle; Y is an amide group wherein Y is $-NHC(=O)-$; $-NHS(=O)_2-$ or $-NHP(=O)<$; q is 1 when Y is $-NHC(=O)-$ or $-NHS(=O)_2-$ and q is 2 when Y is $-NHP(=O)<$; and each R is independently selected from the group consisting of fluoride, chloride, bromide, and substituted or unsubstituted alkyl and aryl groups. A linking group may be employed in which case the following formula is applicable:

$$-LArY[CF_2R]_q$$

wherein L is a linking group comprising a chain containing one or more elements or groups selected from the group consisting of —O—, —S—, —NHC(=O)—, and substituted or unsubstituted alkyl and aryl groups and Ar, Y, R and q are as defined earlier.

The inhibitor fragment of the molecule ("Inh") may be shown in conjunction with the above functionalities in the following formula for the inhibitor moiety:

—Inh—(L)$_m$ArY[CF$_2$R]$_q$ wherein L is a linking group as defined above; m is 0 or 1; and Inh is a heterocyclic fragment which, when combined with Ar (with or without a link,) forms the inhibitor moiety. Where it is desired that the releasable moiety include a timing group designed to delay the inhibiting effect of the inhibitor moiety thus permitting increased mobility, the following formula is representative:

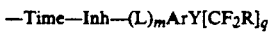
—Time—Inh—(L)$_m$ArY[CF$_2$R]$_q$ wherein Time is one or more timing groups. When considering the overall molecule responsible for the release of the inhibitor moiety, the following formula is appropriate:

COUP—(Time)$_k$—Inh—(L)$_m$ArY[CF$_2$R]$_q$ wherein COUP is a group capable of permitting release of the releasable moiety as a function of development, Time is a timing group, and k is 0 to 3.

The development inhibitor releasing (DIR) compounds of the invention are well known in the art. Typically, these DIR compounds are made up of a carrier or coupler moiety ("COUP") and a releasable moiety containing an inhibitor moiety. The releasable moiety includes any timing groups and the inhibitor moiety which may in turn contain a linking group, an inhibitor fragment, and the amide substituent group in accordance with the invention. The DIR compound reacts with oxidized color developer which effects the release of the inhibitor moiety (including any timing groups, link and the amide group in accordance with the invention.) This inhibitor moiety then migrates during development in order to permit the inhibitor fragment (Inh) and integral amide substituent to suppress development at the desired remote location.

Typically, the compound contains a carrier group (COUP) from which the inhibitor moiety is released either directly or from at least one intervening timing group that is first released from the carrier group.

COUP groups useful in DIR compounds of this invention include various known groups from which the development inhibitor moiety can be released by a variety of mechanisms. Representative COUP groups are described in, for example, U.S. Pat. No. 3,227,550 and Canadian Patent 602,607 (release by chromogenic coupling); U.S. Pat. No. 3,443,939 and 3,443,940 (release by intramolecular ring closure); U.S. Pat. Nos. 3,628,952; 3,698,987; 3,725,062; 3,728,113; 3,844,785; 4,053,312; 4,055,428; and 4,076,529 (release after oxidation of the carrier); U.S. Pat. Nos. 3,980,479; U.K. Patent No. 1,464,104 and 1,464,105 and U.S. Pat. No. 4,199,355 (release unless carrier is oxidized); and U.S. Pat. No. 4,139,379 (release after reduction of the carrier).

Couplers which form magenta dyes upon reaction with oxidized color developing agent are, for example, pyrazolones, pyrazolotriazoles, pyrazolobenzimidazoles and indazolones. Representative couplers are described in such patents and publications as U.S. Pat. Nos. 2,600,788, 2,369,489, 2,343,703, 2,311,082, 2,673,801, 3,152,896, 3,519,429, 3,061,432, 3,062,653, 3,725,067 and 2,908,573 and "Farbkupplereine Literaturubersicht, " published in Agfa Mitteilungen, Band II, pp. 126-156 (1961).

Couplers which form yellow dyes upon reaction with oxidized color developing agent are, for example, acylacetanilides such as benzoylacetanilides and pivaloylacetanilides. Representative couplers are described in the following: U.S. Pat. Nos. 2,875,057, 2,407,210, 3,265,506, 2,298,443, 3,048,194 and 3,447,928 and "Farbkupplereine Literaturubersicht," published in Agfa Mitteilungen, Band II, pp. 112-126 (1961).

Couplers that form cyan dyes upon reaction with oxidized color developing agents are typically phenols and naphthols. Representative couplers are described, for example, in the following: U.S. Pat. Nos. 2,772,162, 2,895,826, 3,002,836, 3,034,892, 2,474,293, 2,423,730, 2,367,531 and 3,041,236 and "Farbkupplerein Literaturubersicht," published in Agfa Mitteilungen, Band II, pp. 156-175 (1961).

DIR compounds that are capable of forming a dye that is colorless and/or capable of being washed out of the photographic silver halide material upon photographic processing are sometimes desirable. Such couplers typically comprise at least one water-solubilizing group on the parent coupler group, such as described in U.S. Pat. No. 4,482,629 and copending application Ser. No. 893,285 of Begley et al, filed Jun. 4, 1992, the disclosures of which are incorporated herein by reference.

The coupler moiety can be ballasted or unballasted. It can be monomeric, or it can be dimeric, oligomeric, or a polymeric coupler, in which case more than one group containing the development inhibitor group can be contained in the coupler.

It will be appreciated, depending upon the particular coupler moiety, the particular color developing agent and the type of processing, the reaction product of the coupler moiety and the oxidized color developing agent can be: (1) colored and nondiffusible, in which case it will remain in the location in which it is formed; (2) colored and diffusible, in which case it may be removed during processing from the location where it is formed or allowed to migrate to a different location, or (3) colorless and diffusible or nondiffusible in which case it will not contribute to image density.

The inhibitor portion of any DIR compound that is useful in the photographic art can be prepared to contain the described amide group so as to function in accordance with the invention. Especially suitable as the inhibitor fragment to be included in the inhibitor moiety are azoles such as triazoles and tetrazoles; benzotriazoles; mercaptoazoles; mercaptooxazoles and mercaptothiazoles.

When the DIR compound is an inhibitor releasing hydroquinone developing agent of the type disclosed in, for example, U.S. Pat. No. 3,379,529, the development inhibitor is imagewise released as a result of silver halide development by the developing agent, optionally in the presence of an auxiliary developing agent. When the DIR compound is a hydroquinone compound of the type described in, for example, European Patent Application NO. 167,168, the development inhibitor is released by a redox reaction in the presence of an oxidized developing agent. Examples of compounds of this type are as follows:

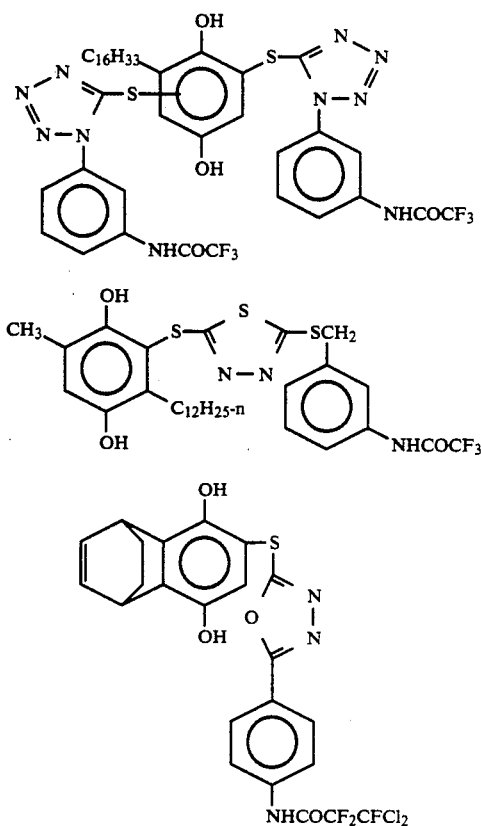

The DIR compounds as described can be used in ways and in materials in which DIR compounds have been used in the photographic art. The term DIR compound herein includes compounds that contain one or more timing groups that enable timing of release of the inhibitor group as well as those that do not contain such a timing group. Any timing group or combination of timing groups known in the photographic art can be useful with the DIR compounds as described. Time may be any organic group which will serve to connect COUP to the inhibitor moiety and which, in turn, after cleavage from COUP, will be cleaved from the inhibitor moiety. For instance, this cleavage may be by an intramolecular nucleophilic displacement reaction of the type described in, for example, U.S. Pat. No. 4,248,962, or by electron transfer along a conjugated chain as described in, for example, U.S. Pat. No. 4,409,323. Examples of —Time—Inh— groups are as follows:

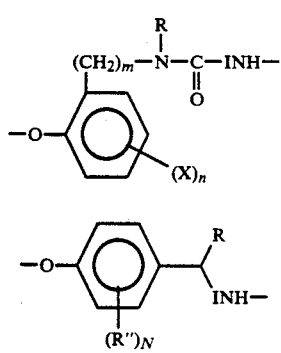

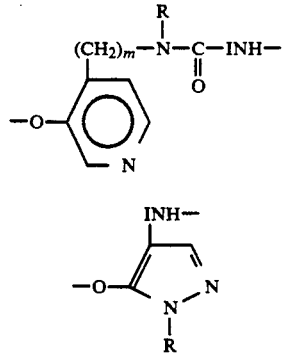

where $m=0$ to 6; $n$ is 0 to 4; each R is independently H or substituted or unsubstituted alkyl or aryl, preferably of less than 30 carbon atoms, X is, for example, hydrogen, a ballast, cyano, fluoro, chloro, bromo, iodo, nitro, alkyl of 1 to 20 carbon atoms, a dye, —OR', —COOR', —CONHR', —NHCOR', NHSO$_2$R', —SO$_2$NHR', or SO$_2$R' where R' is hydrogen, or substituted or unsubstituted alkyl or aryl; and R" is halogen, alkyl, alkoxy, cyano, nitro, carbonamido, or carboxyl. The thiophenols corresponding to these phenols may also be employed.

The releasable development inhibitor moiety is joined to the coupler moiety at the coupling position of the coupler moiety and may be connected through a timing group and/or linking group if present in the inhibitor moiety. Typical Inh groups are heterocyclic rings having 5 or 6 atoms in a monocyclic ring or from 8 to 10 atoms in a bicyclic ring system. The ring includes one or more hetero atoms of nitrogen, sulfur, and oxygen. Such rings include but are not limited to oxazoles, thiazoles, oxathiazoles, diazoles, oxadiazoles, thiadiazoles, thiatriazoles, benzotriazoles, tetrazoles, benzimidazoles, indazoles, isoindazoles, mercaptotetrazoles, selenotetrazoles, mercaptobenzothiazoles, selenobenzoxazoles, mercaptobenzimidazoles, selenobenzimidazoles, benzodiazoles, mercaptooxadiazoles, mercaptothiadiazoles, and benzisodiazoles. Examples of Inh groups are as follows:

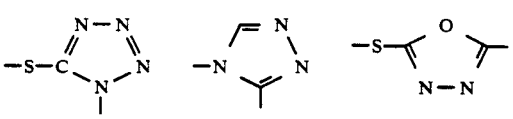

Also useful are inhibitor fragments having sulfur-containing chains in which the Inh substituent contains one or more thioether atoms and where the sulfur atom is directly bonded to a saturated carbon atom but is not directly bonded to an Inh heterocyclic ring as more fully described in U.S. Pat. No. 5,006,448.

The linking group L comprises one or more elements or groups selected from the group consisting of —O—, —S—, —NHCO , and substituted or unsubstituted alkyl and aryl groups. Preferably, when present, the group contains not more than 30 carbon atoms, and is typically an alkylene group of up to 6 carbon atoms. The Ar group may be any aromatic hydrocarbon or heterocycle, preferably phenyl or naphthyl which may be substituted or unsubstituted and preferably contains less than 30 carbon atoms.
Examples of suitable development inhibitor moieties are:
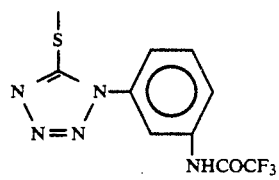
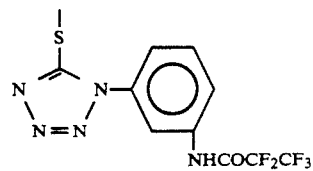
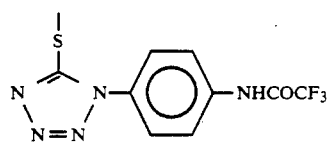
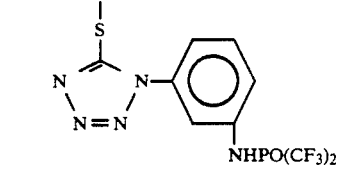
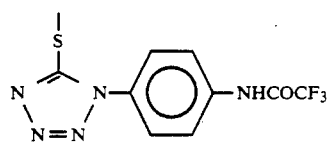
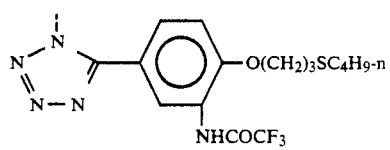
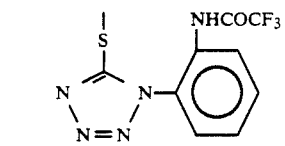
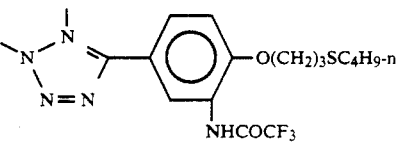
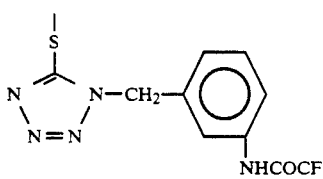
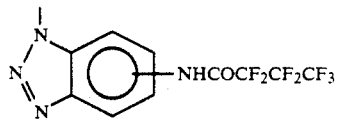
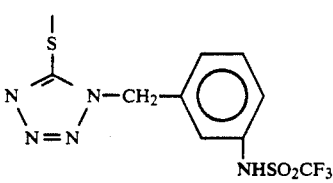
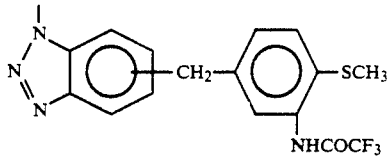
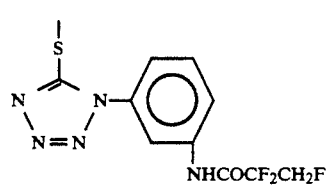
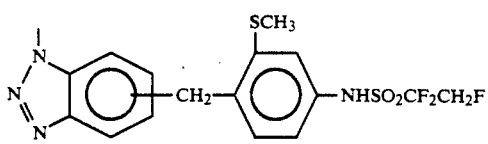
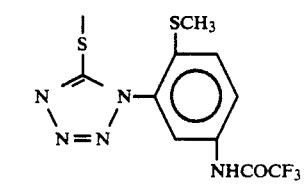
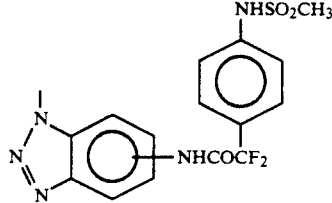

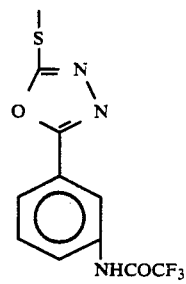
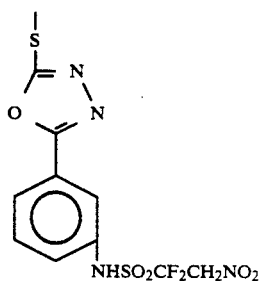
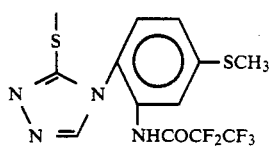
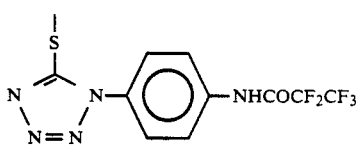
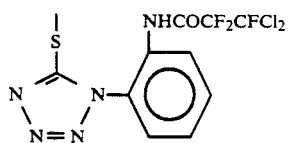
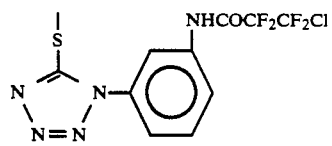
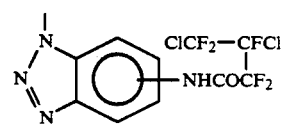
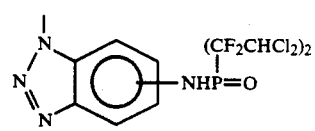
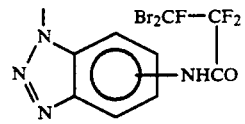
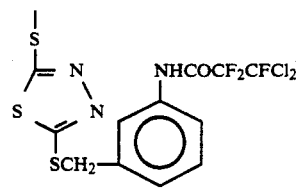
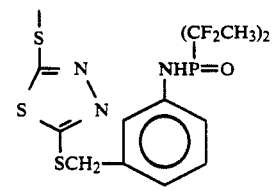
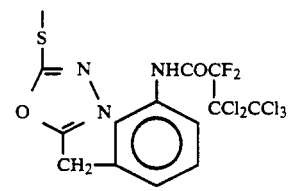
Especially preferred DIR compounds as described are DIR couplers represented by the formulas:
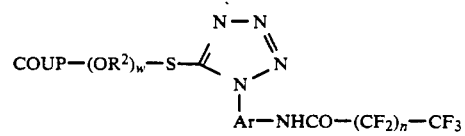
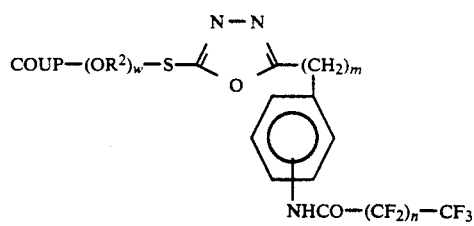
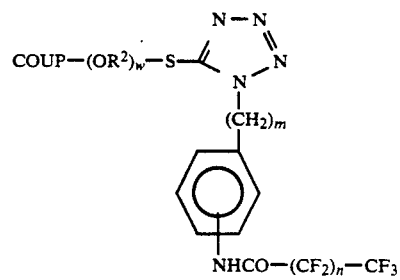

-continued

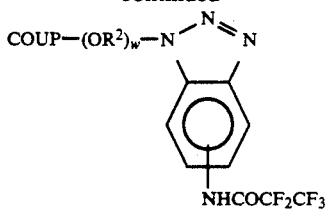

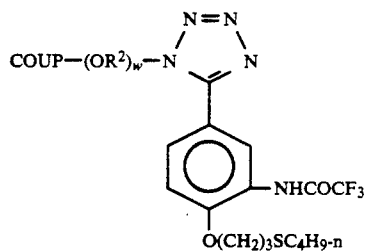

wherein:
COUP is a coupler moiety with the remainder of the molecule substituted in the coupling position, such as a cyan, magenta or yellow coupler moiety known in the photographic art;
$R^2$ is an unsubstituted or substituted aryl group, such as an unsubstituted or substituted phenyl or naphthyl group;
Ar is an arylene group, such as an arylene group containing 6 to 10 carbon atoms, such as phenylene or naphthylene;
m, and n individually are 0, 1 or 2; and,
w is 0 or 1.

Illustrative examples of DIR couplers are as follows:

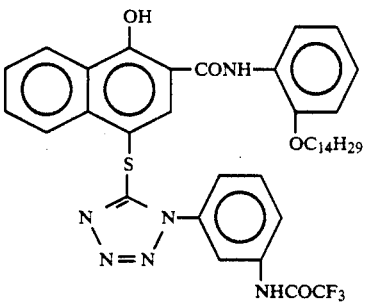

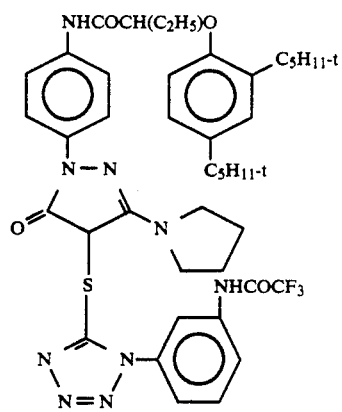

CYAN COUPLER EXAMPLES:

-continued

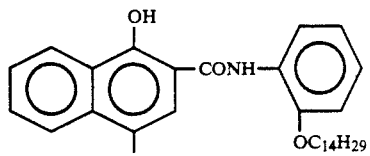

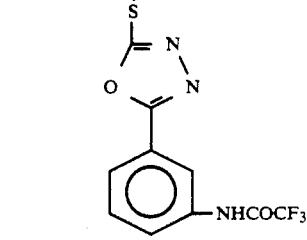

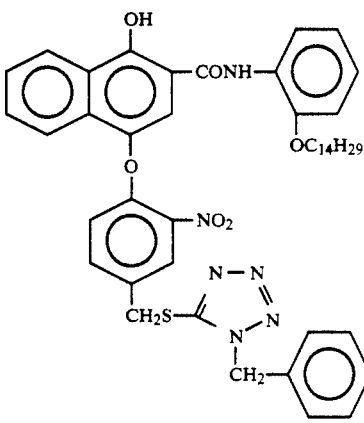

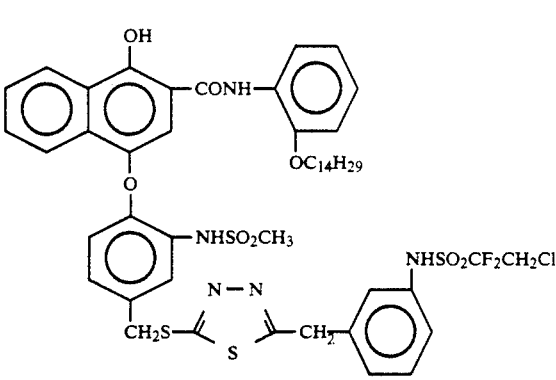

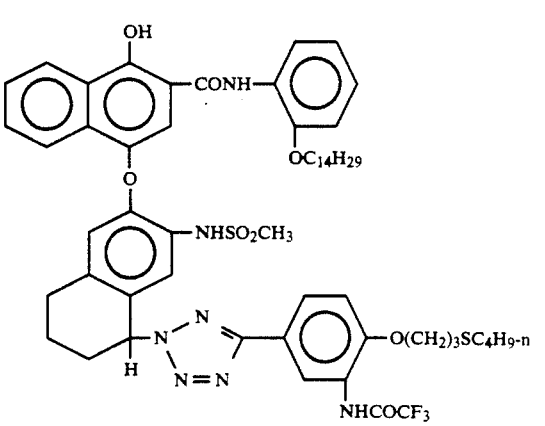

-continued
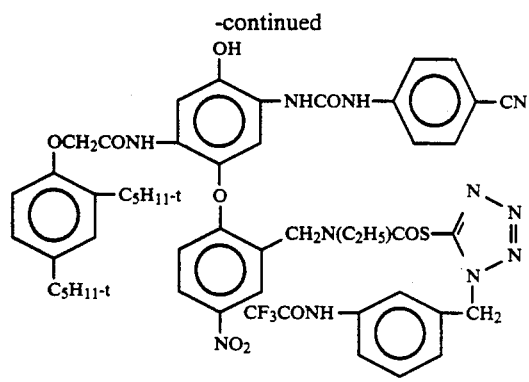
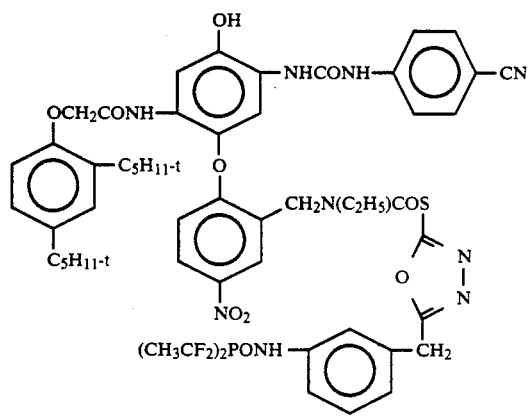
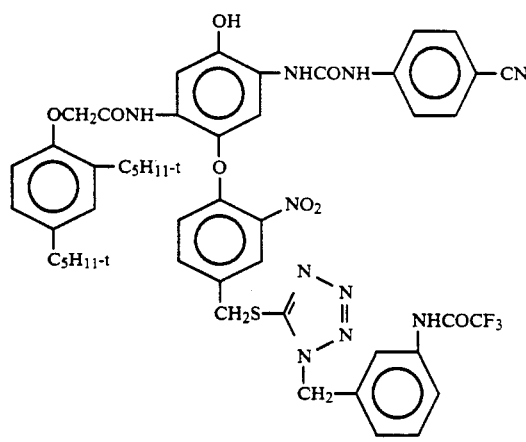
MAGENTAS:
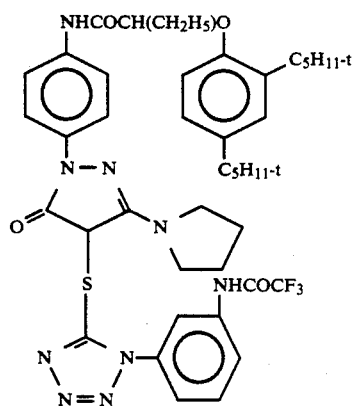
-continued
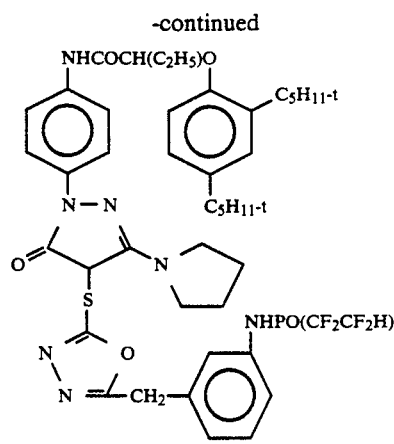
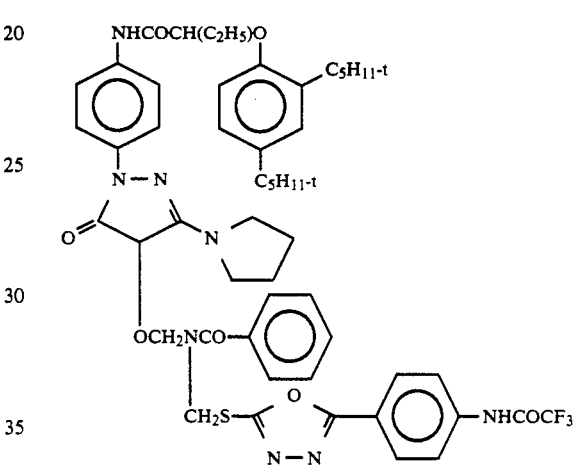
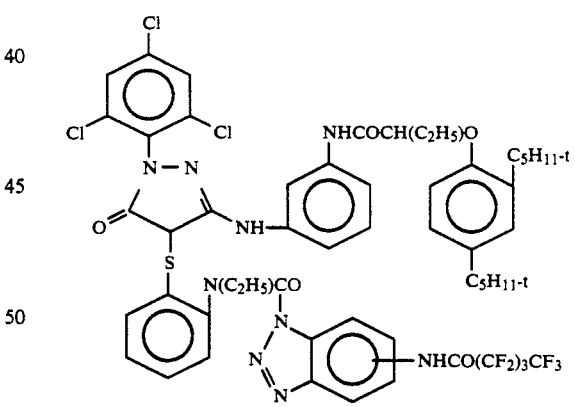
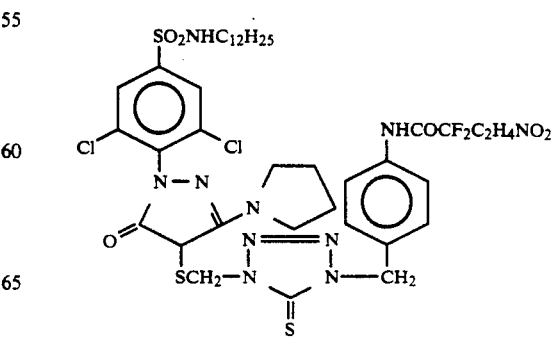

-continued
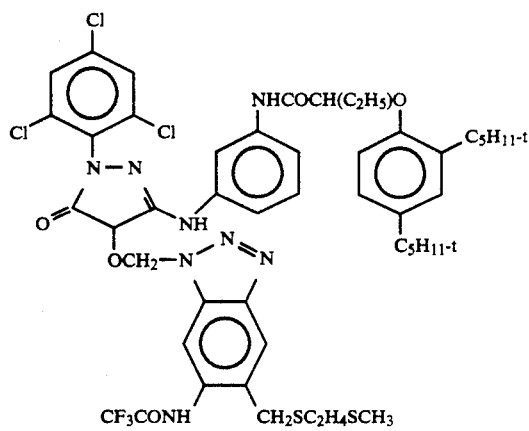
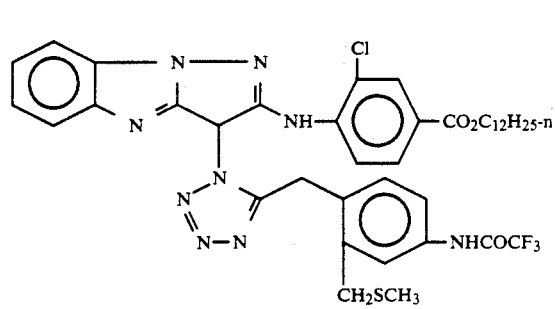
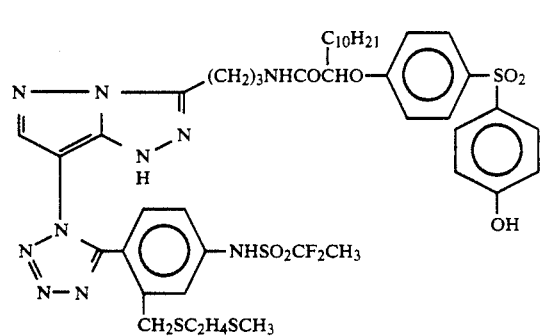
YELLOWS:
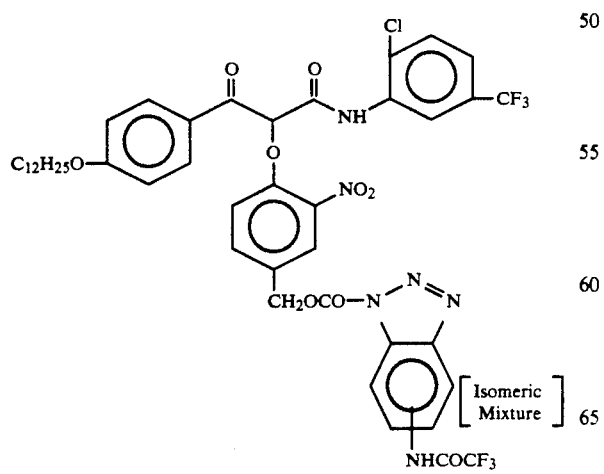
-continued
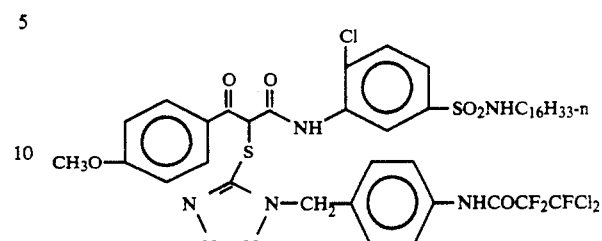
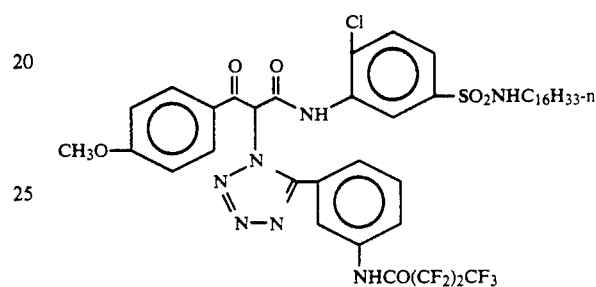
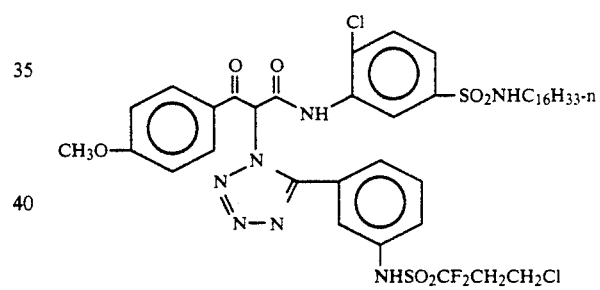

-continued

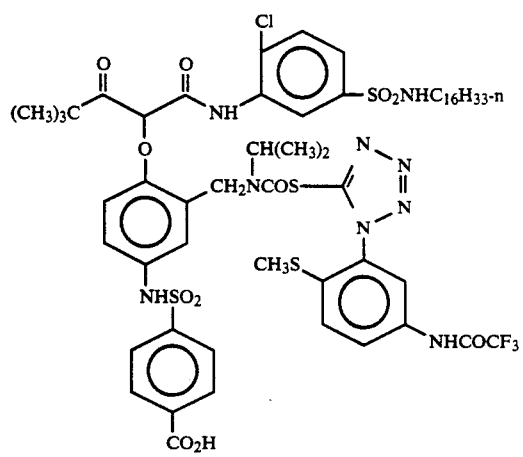

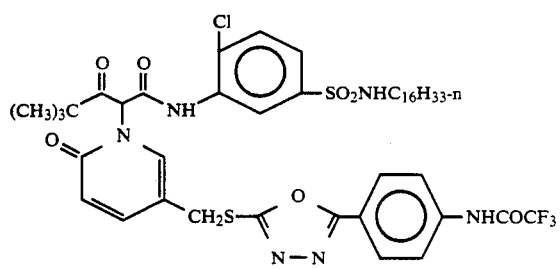

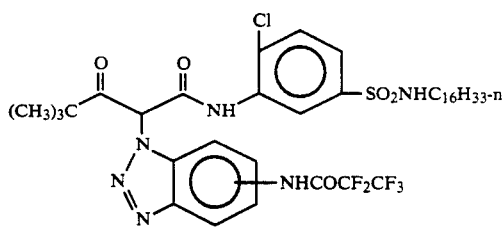

UNIVERSALS:

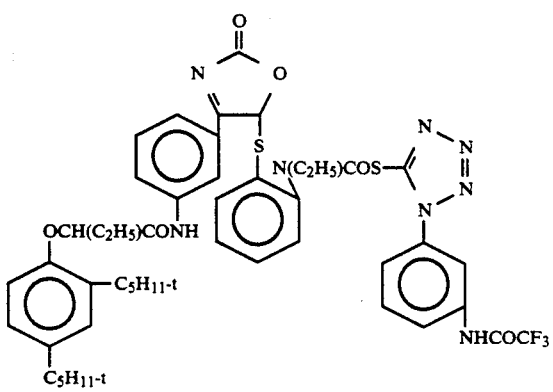

-continued

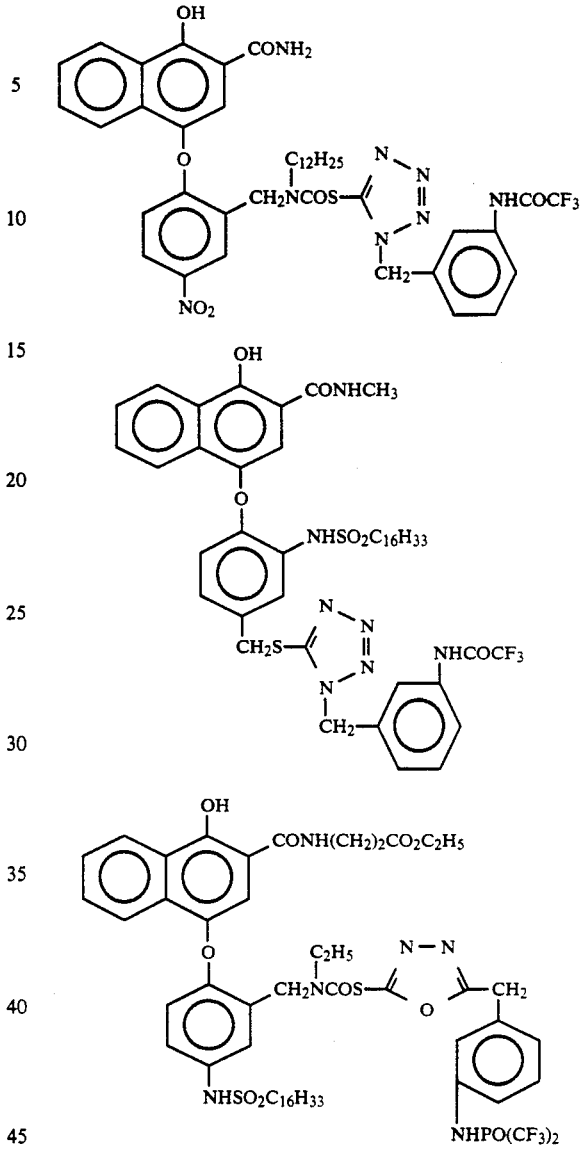

The DIR compounds of the invention can be incorporated in photographic elements by means and processes known in the photographic art. In a photographic element prior to exposure and processing the DIR coupler should be of such size and configuration that it will not diffuse through the photographic layers.

Photographic elements of the invention can be processed by conventional techniques in which color forming couplers and color developing agents are incorporated in separate processing solutions or compositions or in the element.

Photographic elements, in which the DIR compounds of the invention can be incorporated, can be a simple element comprising a single silver halide emulsion layer or they can be multilayer, multicolor elements. The DIR compounds of the invention can be incorporated in at least one of the silver halide emulsion layers and/or in at least one of the other layers of the element, such as an adjacent layer, where they will come into reactive association with oxidized developing agent which has developed silver halide in the emulsion layer. The silver halide emulsion layer can have in it or have associated with it, other photographic coupler compounds, such as dye-forming couplers, colored masking couplers, and/or competing couplers. These other photographic couplers can form dyes of the same or different color and hue as the DIR couplers of the invention. Additionally, the silver halide emulsion layers and other layers of the photographic element can contain addenda conventionally contained in such layers.

A typical multilayer, multicolor photographic element can comprise a support bearing a red-sensitive silver halide emulsion unit having associated therewith a cyan dye image-providing material, a green-sensitive silver halide emulsion unit having associated therewith a magenta dye image-providing material, and a blue-sensitive silver halide emulsion unit having associated therewith a yellow dye image-providing material, at least one of the silver halide emulsion units having associated therewith a DIR compound, preferably a DIR coupler, of the invention. Each silver halide emulsion unit can be composed on one or more layers and the various units and layers can be arranged in different locations with respect to each other.

The DIR couplers of the invention can be incorporated in or associated with one or more layers or units of the photographic element. Combinations of DIR couplers of the invention can be used. Also, combinations of DIR couplers of the invention with at least one DIR coupler known in the photographic art can be used in the photographic element. At least one of the layers of the photographic element can be, for example, a mordant layer, a barrier layer, an inhibitor scavenger layer or the like.

The light sensitive silver halide emulsions can be any of those known in the photographic art. They can be coarse, regular or fine grain silver halide crystals or mixtures thereof and can be comprised of such silver halides as silver chloride, silver bromide, silver bromoiodide, silver chlorobromide, silver chloroiodide, silver chlorobromoiodide, and mixtures thereof. The emulsions can be negative-working or direct-positive emulsions. They can form latent images predominantly on the surface of the silver halide or predominantly on the interior of the silver halide grains. They can be chemically and spectrally sensitized. The emulsions typically will be gelatin emulsions although other hydrophilic colloids are useful. Tabular grain light sensitive silver halides are particularly useful, such as described in Research Disclosure, January, 1983, Item No. 22534 and U.S. Pat. No. 4,434,226.

If desired, the photographic element can be used in conjunction with an applied magnetic layer as described in *Research Disclosure*, November 1992, Item 34390 published by Kenneth Mason Publications, Ltd., Dudley Annex, 12a North Street, Emsworth, Hampshire P010 7DQ, ENGLAND.

In the following discussion of suitable materials for use in the emulsions and elements of this invention, reference will be made to Research Disclosure, December 1989, Item No. 308119, available as described above. This publication is identified hereinafter by the term "Research Disclosure".

The photographic elements can be coated on a variety of supports as described in Research Disclosure Section XVII and the references described therein.

Photographic elements can be exposed to actinic radiation, typically in the visible range of the electromagnetic spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with an image dye-forming coupler to yield a dye. The oxidized color developing agent also reacts with the DIR coupler present.

Preferred color developing agents useful in the invention are p-phenylenediamines. Especially preferred are 4-amino-N,N-diethylaniline hydrochloride; 4-amino-3-methyl-N,N-diethylaniline hydrochloride; 4-amino-3-methyl-N-ethyl-N-o-(methanesulfonamido)ethylaniline sulfate hydrate; 4-amino-3-methyl-N-ethyl-N-o-hydroxyethylaniline sulfate; 4-amino-3-o-(methanesulfonamido)-ethyl-N,N-diethylaniline hydrochloride; and 4-amino-N-ethyl-N-(2-methoxyethyl)-m-toluidine di-p-toluenesulfonic acid.

The described photographic materials and processes can be used with the photographic silver halide emulsions and addenda known to be useful in the photographic art, as described in, for example, the Research Disclosure publication, the disclosures of which are incorporated herein by reference.

With negative silver halide, the processing step described above provides a negative image. To obtain a positive image (or reversal image), this step can be preceded by development with a non-chromogenic developing agent to develop exposed silver halide, but not form a dye, and then uniformly fogging the element to render unexposed silver halide developable. Alternatively, a direct positive emulsion can be employed to obtain a positive image.

Development is followed by the conventional steps of bleaching, fixing, or bleach-fix, to remove silver and silver halide, washing and drying.

DIR compounds as described can be prepared by reactions and methods known in the organic compound synthesis art. Typically the DIR compounds are simply prepared by reacting the parent carrier compound, especially the parent coupler, with the thiol form of the development inhibitor moiety. The following description illustrates these syntheses:

Synthesis Example A:

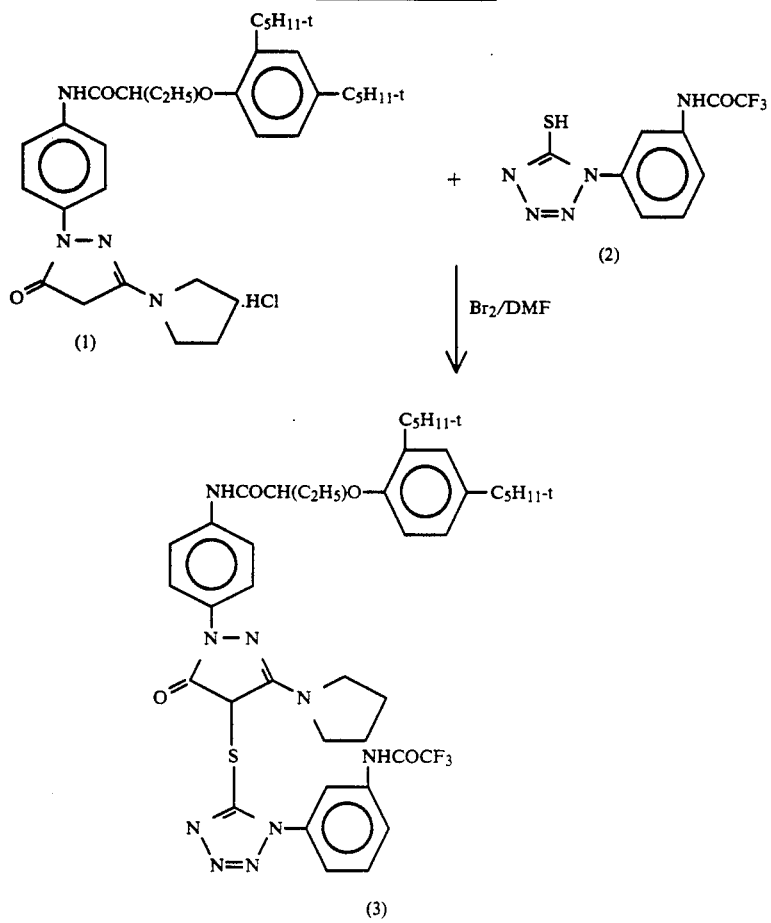

To a solution of the 2-arylpyrazolone (1) (58.3 g, 0.1 mole) and the mercaptotetrazole (2) (28.9 g, 0.1 mole) in 350 ml DMF was added bromine (16.0 g., 0.1 mole) at 5° to 10° C. The resulting solution was stirred at ambient temperature (20° C.) for 20 hours and then poured into 2000 g of ice. The precipitated product was filtered, washed with water, heptane and vacuum dried. The product was taken up in 2% methanol in dichloromethane and chromatographed over silica gel eluting with the same solvent. The product was further purified by recrystallization from 750 ml of hot acetonitrile and digested with 400 ml of hot methanol. The product yield was 83% (69.0 g.). The product was identified by elemental analysis and NMR and had a melting point of 171° C.

Synthesis Example B:

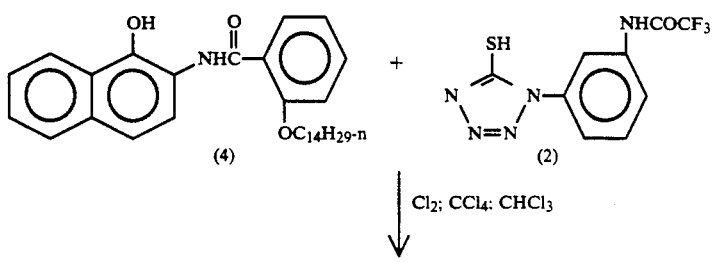

Synthesis Example B:

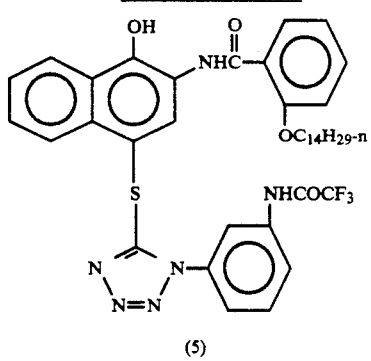

(5)

Chlorine gas (1.5 g, 0.0211 mole) was bubbled through a suspension of mercaptotetrazole (2) (4.5 g, 0.0156 mole) in chloroform. The resulting solution was added to a solution of the 1-hydroxynaphthalene (4) in warm (50° C.) carbon tetrachloride and the mixture was refluxed for 5 minutes, filtered hot and the filtrate set aside for 20 hours. The precipitate was collected and recrystallized from methanol. The desired product (5) was identified by elemental analysis and NMR. The product was produced in 21% yield (2.4 g.) and had a melting point of 148° C.

-continued thane/10 ml trifluoroacetic acid was kept at room trmperature for 30 minutes, concentrated in vacuo, and the residue was purified by chromatography over silica gel eluting with heptane/dichloromethane (3/7). The product was rectystallized from methanol giving 4.87 g (51%) of the product (8), melting point 105°-106° C. It had a correct NMR and elemental analysis.

Synthesis Example C:

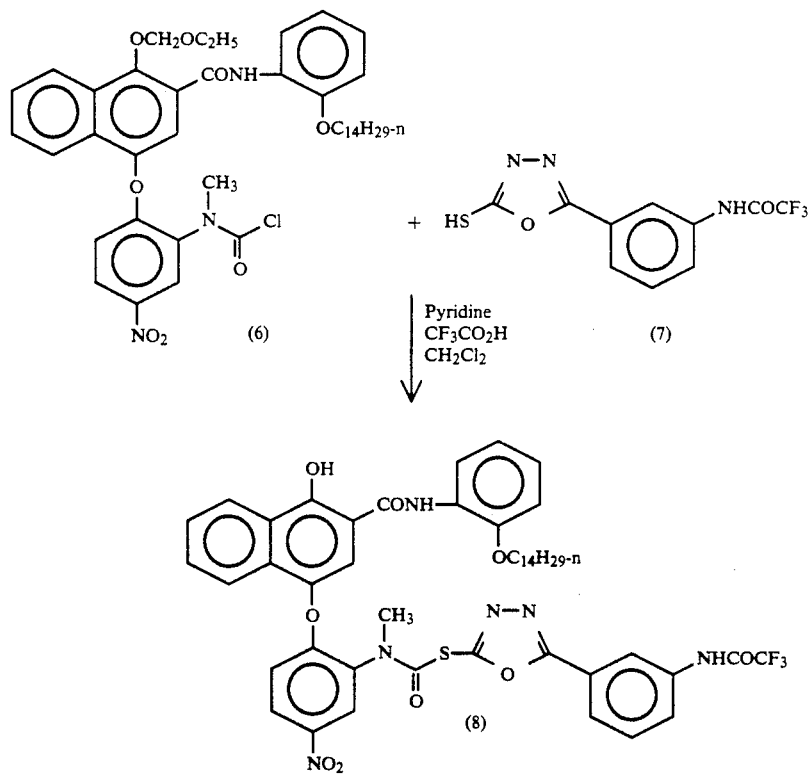

To a solution of the carbamoyl chloride (6) (7.62 g; 10 mmole) in 30 ml pyridine was added at 5° C. solid mercaptooxadiazole (7) over a period of 15 minutes. The resulting solution was stirred at ambient temperature for 15 minutes and then partitioned between ethyl acetate and 5% aqueous hydrochloric acid. The organic sloution was extracted with brine, dried, and concentrated to an oil. A solution of this oil in 100 ml dichlorome-

Synthesis Example D:

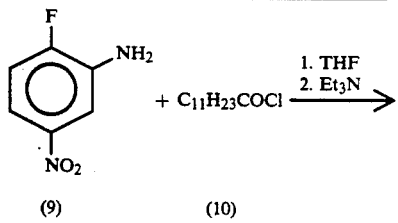

(9)  (10)

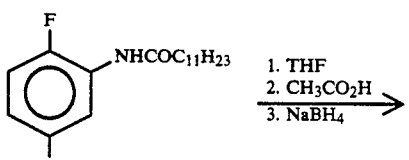

(11)

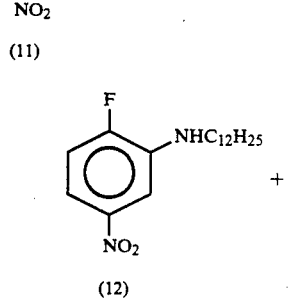

(12)

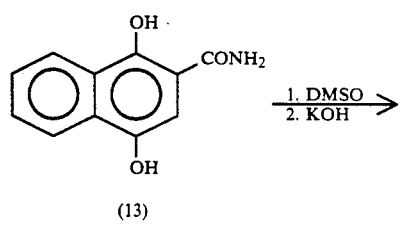

(13)

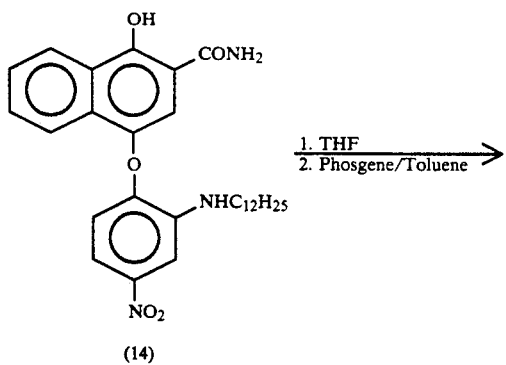

(14)

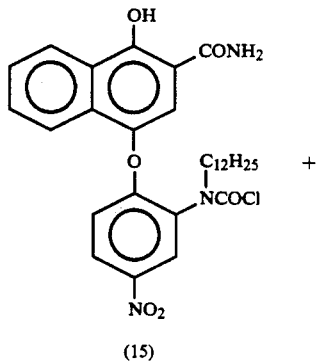

(15)

-continued
Synthesis Example D:

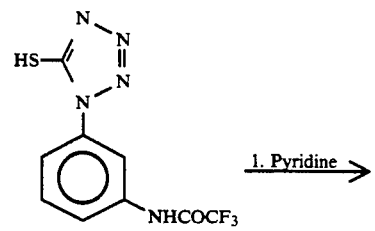

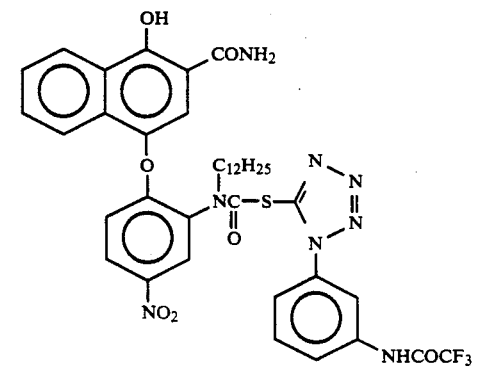

The 2-fluoro,5-nitroaniline was dissolved in THF with triethylamine and treated dropwise with lauroyl chloride. A thick precipitate came out of solution during addition. This stirred at room temperature for 30 minutes. The triethylamine salt was filtered and washed with THF. The solvent was removed under reduced pressure and the resulting oil was slurried in high boiling ligroin. The cream colored solid is filtered and air dried to give 36.7 grams (72%) of the amide. NMR is consistent with the expected structure.

The amide was dissolved in THF and cooled to 0 to 5 degrees C. with an ice/acetone bath. Sodium Borohydride was added portionwise to the THF to form a thick slurry. When all the foaming and bubbling have stopped the reaction was slowly heated to reflux for 2.5 hours. At this point the solution was slowly poured into 1500 ml of cold 10% HCl. When the foaming and bubbling stop, the product is extracted into ethyl acetate, the organic layers are combined and dried with magnesium sulfate. The solvents are removed under reduced pressure to give a yellow oil. This is dissolved in low boiling ligroines and chromatographed with ligroines. The final oil obtained is dissolved in low boiling ligroines and cooled in a dry ice/acetone bath. The solid that comes out of solution is filtered and air dried to give 22.6 grams (64%) of a yellow solid. NMR is consistent with the expected structure.

The 1,4-naphthamide is dissolved in DMSO with the 2-fluoro-5-nitro-N-dodecylaniline, and treated in one portion with two equivalents of potassium hydroxide in water. The dark solution was allowed to stir at room temperature for four hours. TLC shows one major new material and five or six small impurities. The reaction product was poured onto a mechanically stirred solution of ice cold 10% HCl (1 liter). To this mixture, 400 ml of ethyl acetate was added. The solid which came out of solution was filtered and air dried overnight. This gave 44 grams (47%) of a dark green solid, mainly one spot of TLC. NMR is consistent with the expected structure.

The amine was dissolved in 600 ml of THF and treated in one portion with three equivalents of 15% phosgene in toluene. After one hour the solvent was removed under reduced pressure and the dark oil remaining was slurried in 500 ml of ethyl ether. The solid which formed was filtered and air dried to give 39.7 grams (79%) of a greenish solid. The carbamoyl chloride is taken on without further purification to the next step.

The carbamoyl chloride was dissolved in 100 ml of pyridine treated with trifluoroacetamidophenylmercaptotetrazole and stirred at room temperature for three hours. The reaction product was then poured into 600 ml of 10% HCl and extracted with ethyl acetate. The organic layers were combined, dried with magnesium sulfate, filtered and the solvents removed under reduced pressure. The green oil was then dissolved in dichloromentane and chromatographed, eluting with $CH_2Cl_2$/EtOAc (90/10). The oil obtained was dissolved in ether and treated with low boiling ligroines until the solution became cloudy. The light yellow solid which formed was filtered and air dried to give 9.8 grams (55%) of product. TLC=EtOAc 30%, Heptane 70%. NMR is consistent with the structure as was the combustion analysis.

The following examples further illustrate the invention:

EXAMPLE 1

Photographic elements were prepared by coating the following layers on a cellulose ester film support (amounts of each component are indicated in mg/m²):

| | |
|---|---|
| Emulsion layer 1: (Receiver Layer) | Gelatin - 2420; red sensitized silver bromoiodide (as Ag) - 1615; yellow image coupler dispersed in dibutyl phthalate |
| Interlayer: | Gelatin - 860 didodecylhydroquinone - 113 |
| Emulsion layer 2: (Causer Layer) | Gelatin - 2690; green sensitized silver bromoiodide (as Ag) - 1615; magenta image coupler dispersed in tritolylphosphate; DIR compound of Table I dispersed in N,N-diethyl-dodecanamide and coated at a level sufficient to provide a contrast of 0.5 (half) of the original contrast after stepwise green light exposure and processing |
| Protective Overcoat | Gelatin - 5380 bisvinylsulfonylmethyl ether at 2% total gelatin |

Magenta Image Coupler:

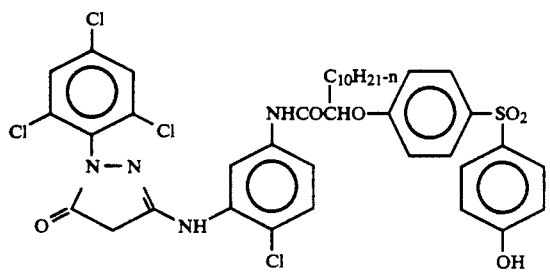

Yellow Image Coupler:

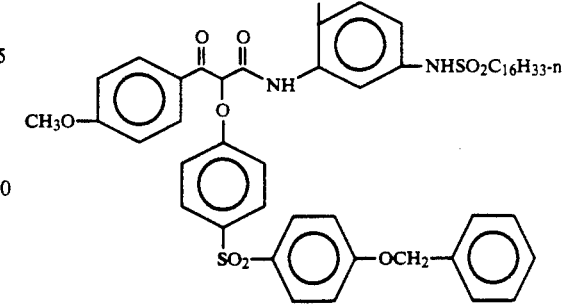

Strips of each element were exposed to green light through a graduated density step tablet, or through a 35% modulation fringe chart for sharpness measurements, and then developed 3.25 minutes at 38° C. in the following color developer, stopped, washed, bleached, washed, fixed, washed and dried.

| Color Developer: | |
|---|---|
| Sodium Metabisulfite | 2.78 g |
| Sodium Sulfite, anhydrous. | 0.38 g |
| Kodak Color Developer CD-4 | 4.52 g |
| Potassium Carbonate, anhyd. | 34.3 g |
| Potassium Bicarbonate | 2.32 g |
| Sodium Bromide | 1.31 g |
| Potassium Iodide | 1.20 mg |
| Hydroxylamine Sulfate (HAS) | 2.41 g |
| Diethylenetriaminepentacetic acid, pentasodium salt (40% Soln.) | 8.43 g |
| Distilled water | to 1 L |
| Adjust pH to 10.0. | |

*CD-4 is 4-amino-3-methyl-N-ethyl-N-beta-hydroxy-ethylaniline sulfate.

Processed images were read with green light to determine the sensitometric response of the causer layer. From this the contrast was calculated. AMT acutance determinations were also made. From plots of AMT acutance vs. The logarithm of the contrast for variations in the coated level of each development inhibitor releasing (DIR) compound, the acutance was determined at a contrast of approximately 0.5 compared to its original contrast without the presence of the DIR compound. The acutance for the control DIR coupler at this point was subtracted from each AMT value to provide the relative sharpness value reported as change in AMT in Table I. Tables II and III use the AMT values measured at the stated contrast reductions. AMT calculations employed the following formula in which the cascaded area under the system modulation curve is shown in equation (21.104) on page 629 of the "Theory of the Photographic Process", 4th Edition, 1977, edited by T. H. James: AMT=100+66Log [cascaded area/2.6696M] wherein the magnification factor M is 3.8 for the 35 mm system AMT. The use of CMT acutance is described by R. G. Gendron in "An Improved Objective Method of Rating Picture Sharpness: CMT Actuance" in the Journal of SMPTE, Vol. 82, pages 1009-12, (1973). AMT is a further modification of CMT useful for evaluating systems which include the viewing of a positive print made from a negative.

TABLE I

| Example No./ Coupler No. | Change in AMT | Gamma Causer/ Gamma Receiver |
|---|---|---|
| Control Coupler | 0 | 2.9 |

TABLE I-continued

| Example No./ Coupler No. | Change in AMT | Gamma Causer/ Gamma Receiver |
|---|---|---|
| Comparison | 0 | 3.3 |
| Coupler 1 (Invention) | 1.0 | 3.8 |

Control Coupler:

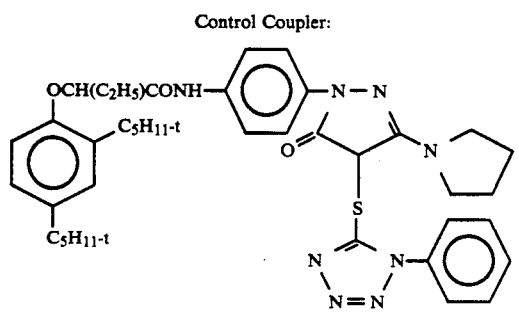

Comparison Coupler:

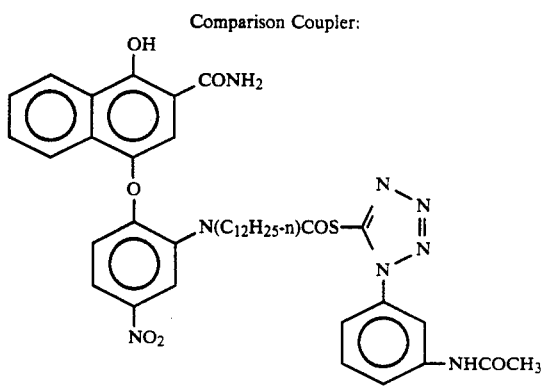

Coupler 1 (Invention):

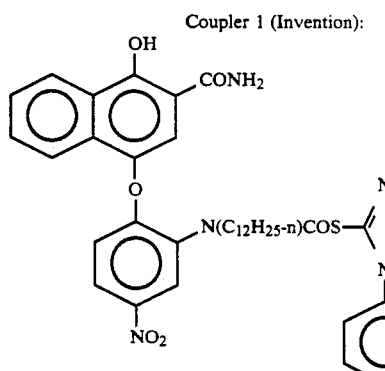

EXAMPLE 2

Example 1 was repeated except that a cyan image coupler of the following structure dispersed in dibutyl phthalate was used in place of the magenta image coupler and DIR compounds of the indicated formulas were tested:

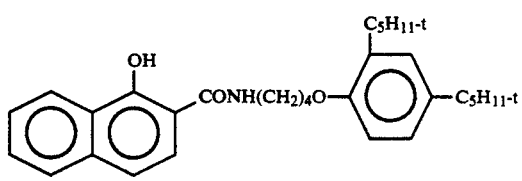

Processed images were read with red light to determine the contrast and AMT acutance.

The coated level of DIR compound was varied in these coatings. The AMT values used to derive the data in Table 2 and 3 was obtained from those coatings in which the presence of the inhibitor, released from the DIR compound resulted in an approximately 50% contrast suppression compared to a coating containing no DIR.

The resulting acutance and contrast data for the control, invention, and comparison DIR's are shown in TAble II.

TABLE II

| Compound No. | Change in AMT | % Causer Gamma Suppression | Causer Gamma/ Receiver Gamma |
|---|---|---|---|
| Control (2) | — | 53 | 1.2 |
| Invention (3) | 2.7 | 59 | 2.4 |
| Comparison (4) | 1.5 | 58 | 1.3 |

EXAMPLE 3

The coating format of Example 2 was repeated using the couplers indicated below:

Control (2):

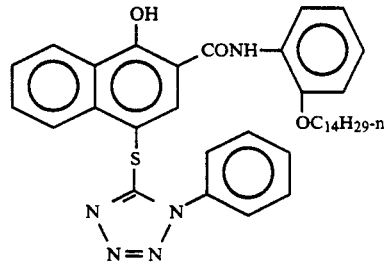

Invention (3):

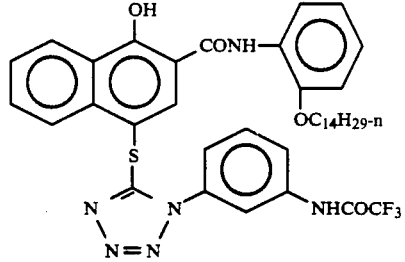

Comparision (4):

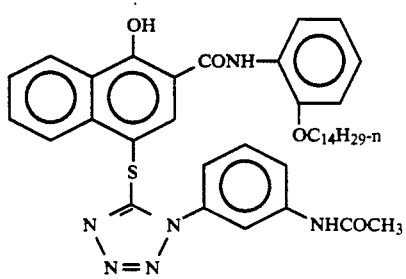

TABLE III

| Compound No. | Change in AMT | % Causer Gamma Suppression | Causer Gamma/ Receiver Gamma |
|---|---|---|---|
| Control (2) | — | 50 | 0.8 |
| Invention (5) | 1.5 | 56 | 1.2 |
| Comparison (6) | 0.8 | 60 | 0.9 |

Invention (5):

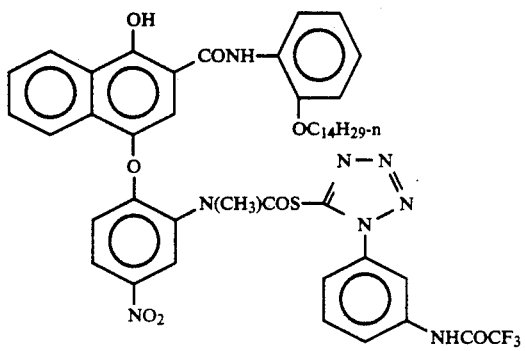

Comparision (6):

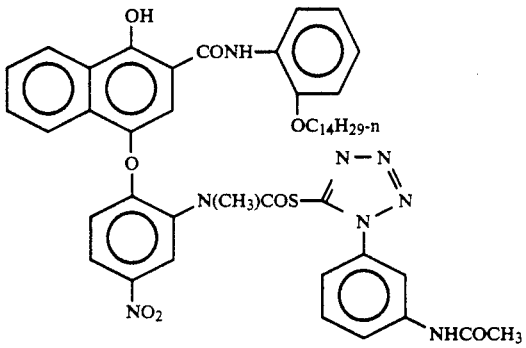

In each example, the compounds of the invention gave higher accutance and more receiver contrast reduction for a given causer contrast reduction (i.e. more interimage effect) than the comparison and control compounds.

The invention has been described in detail with particular reference to preferred embodiments thereof, but it will be understood that variations and modifications can be effected within the spirit and scope of the invention.

What is claimed is:

1. A photographic element comprising at least one photographic silver halide emulsion having associated therewith at least one DIR compound having a releasable moiety which contains a development inhibitor moiety wherein the development inhibitor moiety comprises an amide functionality containing a carbon alpha to the amide functionality which is di- or tri-fluorinated.

2. The element of claim 1 wherein the development inhibitor moiety contains an amide functionality represented by the formula:

—ArY[CF$_2$R]$_q$ wherein Ar is an aromatic hydrocarbon or heterocycle; Y is an amide group selected from the group consisting of —NHC(=O)—; —NHS(=O)$_2$— and —NHP(=O)<; q is 1 when Y is —NHC(=O)— or —NHS(=O)$_2$— and 2 when Y is —NHP(=O)<; and each R is independently selected from the group consisting of fluoride, chloride, bromide, and substituted or unsubstituted alkyl and aryl groups.

3. The element of claim 2 wherein said amide functionality is represented by the formula:

—LArY[CF$_2$R]$_q$ wherein L is a linking group comprising a chain containing one or more elements or groups selected from the group consisting of —O—, —S—, —NHC(=O)—, and substituted or unsubstituted alkyl and aryl groups and Ar, Y, R and q are as defined in said claim.

4. The element of claim 2 wherein said development inhibitor moiety is represented by the formula:

—Inh—(L)$_m$ArY[CF$_2$R]$_q$ wherein L is a linking group comprising a chain containing one or more elements or groups selected from the group consisting of —O—, —S—, —NHC(=O)—, and substituted or unsubstituted alkyl and aryl groups; m is 0 or 1; and Inh is a heterocyclic ring necessary to complete the structure of a development inhibitor moiety and wherein, when m=0, Ar may be attached in Inh at either one or two positions and Ar, Y, R, and q are as defined in said claim.

5. The element of claim 1 wherein the releasable moiety is represented by the formula:

—(Time)$_k$—Inh—(L)$_m$ArY[CF$_2$R]$_q$ wherein Time is a timing group, k is 0 to 3, L is a linking group comprising a chain containing one or more elements or groups selected from the group consisting of —O—, —S—, 'NHC(=O)—, and substituted or unsubstituted alkyl and aryl groups; m is 0 or 1; Inh is a heterocyclic ring necessary to complete the structure of a development inhibitor moiety and wherein, when m=0, Ar may be attached to Inh at either one or two positions; Ar is an aromatic hydrocarbon or heterocycle; Y is an amide group selected from the group consisting of —NHC(=O)—; —NHS(=))$_2$— and —NHP(=O)<; g is 1 when Y is —NHC(=o)— or —NHS (=O)$_2$— and 2 when Y is —NHP(=O)<; and each R is independently selected from the group consisting of fluoride, chloride, bromide, and substituted or unsubstituted alkyl and aryl groups.

6. The element of claim 1 wherein the DIR compound is represented by the formula:

COUP—(Time)$_k$—Inh—(L)$_m$ArY[CF$_2$R]$_q$ wherein COUP is a group capable of releasing the remainder of the molecule upon development, k is 0 to 3; Time is a timing group; L is a linking group comprising a chain containing one or more elements or groups selected from the group consisting of —O—, —S—, —NHC(=O)—, and substituted or unsubstituted alkyl and aryl groups; m is 0 is 1; Inh is a heterocyclic ring necessary to complete the structure of a development inhibitor moiety and wherein, when m=0, Ar may be attached in Inh at either one or two positions; Ar is an aromatic hydrocarbon or heterocycle; Y is an amide group selected from the group consisting of —NHC- (=O)—; —NHS(=O)₂— and —NHP(=O)<; g is 1 when Y is —NHC(=O)— or —NHS(=O)₂— and 2 when Y is —NHP(=O)<; and each R is independently selected from the group consisting of fluoride, chloride, bromide, and substituted or unsubstituted alkyl and aryl groups.

7. The element of claim 6 wherein the DIR compound is selected from the group consisting of

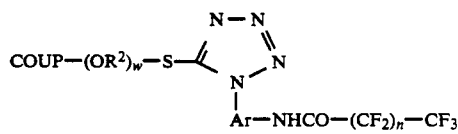

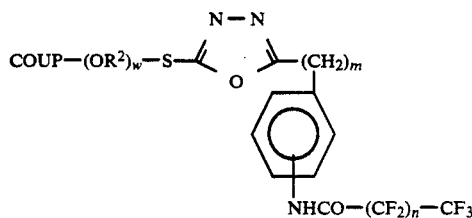

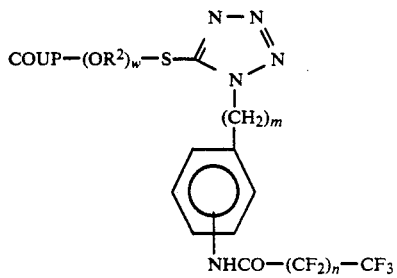

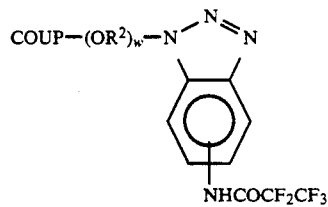

and

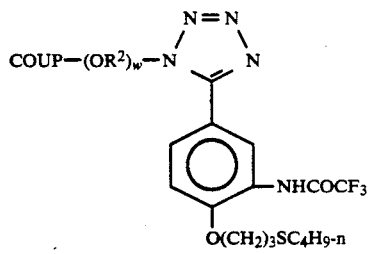

wherein

COUP is a coupler moiety containing the remainder of the molecule substituted in the coupling position;

$R^2$ is an unsubstituted or substituted aryl group;

Ar is an alkylene or arylene group; m is 0 to 6, n is 0 to 3,; and w is 0 or 1.

8. The element of claim 6 wherein the DIR compound is selected from the group consisting of

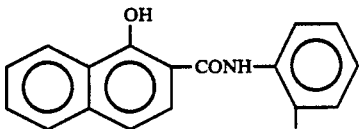

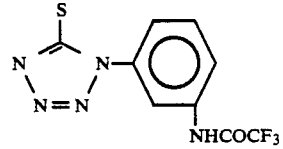

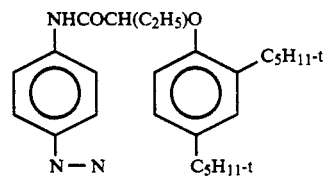

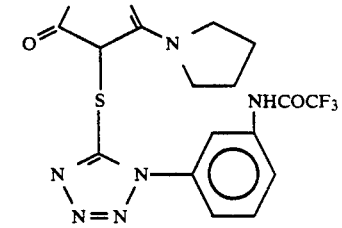

9. The element of claim 1 additionally comprising at least one red-sensitive silver halide emulsion unit having associated therewith a cyan dye image-forming material, at least one green-sensitive silver halide emulsion unit having associated therewith a magenta dye image-forming material, and at least one blue-sensitive silver halide emulsion unit having associated therewith a yellow dye image-forming material, wherein at least one of said silver halide emulsion units contains said DIR compound.

10. The element of claim 2 wherein R is an aryl group having a solubilizing substituent.

11. The element of claim 10 wherein said solubilizing substituent is selected from —OH, —CO₂H, —SO₂NH₂, —SO₂NHCH₃, —SO₂NHCF₃, —NHSO₂CH₃, —NHSO₂CF₃, and a polyalkylene oxide.

12. A process of forming a photographic image in an exposed photographic element comprising developing an element as defined in any one of claims 1 through 11 with a photographic silver halide color developing agent.

* * * * *